United States Patent [19]
Lee

[11] Patent Number: 5,925,755
[45] Date of Patent: Jul. 20, 1999

[54] PROCESS FOR THE PREPARATION OF LAMOTRIGINE

[75] Inventor: Grahame Roy Lee, Dartford, United Kingdom

[73] Assignee: Glaxo Wellcome Inc., Research Triangle Park, N.C.

[21] Appl. No.: 08/836,152

[22] PCT Filed: Dec. 29, 1995

[86] PCT No.: PCT/GB95/03049

§ 371 Date: Jun. 25, 1997

§ 102(e) Date: Jun. 25, 1997

[87] PCT Pub. No.: WO96/20935

PCT Pub. Date: Jul. 11, 1996

[30] Foreign Application Priority Data

Dec. 30, 1994 [GB] United Kingdom ............... 9426448

[51] Int. Cl.⁶ .......................................... C07D 253/075
[52] U.S. Cl. ........................................... 544/182
[58] Field of Search ............................... 544/182

[56] References Cited

FOREIGN PATENT DOCUMENTS 0021121  1/1981  European Pat. Off. .

*Primary Examiner*—John M. Ford
*Attorney, Agent, or Firm*—Nixon & Vanderhye

[57] ABSTRACT

Lamotrigine, 3,5-diamino-6-(2,3-dichlorophenyl)-1,2,4-triazine, may be prepared by treating 6-(2,3-dichlorophenyl)-5-chloro-3-thiomethyl-1,2,4-triazine of formula (II)

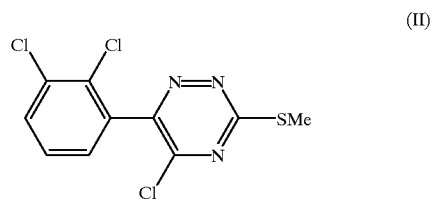

(II)

with ammonia. Precursors to the compound of formula (II), and their preparation, are also described.

8 Claims, No Drawings

PROCESS FOR THE PREPARATION OF LAMOTRIGINE

The present invention relates to a process for the preparation of lamotrigine and its pharmaceutically acceptable acid addition salts.

Lamotrigine is 3,5-diamino-6-(2,3-dichlorophenyl)-1,2,4-triazine, of formula (I)

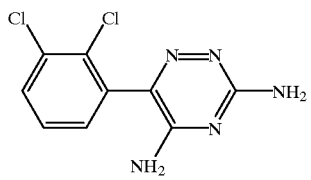

(I)

It is a known compound, useful in the treatment of disorders of the central nervous system (CNS), in particular epilepsy, described for example in EP-A-0021121. Lamotrigine isethionate, disclosed in EP-A-0247892, is a preferred salt for parenteral administration.

The present invention provides a process for the preparation of lamotrigine which comprises treating 6-(2,3-dichlorophenyl)-5-chloro-3-thiomethyl-1,2,4-triazine of formula (II)

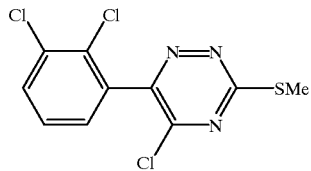

(II)

with ammonia.

The reaction of the compound of formula (II) with ammonia may be carried out in an organic solvent. Suitable solvents include $C_{1-6}$ alkanols, such as methanol, ethanol, propan-1-ol or propan-2-ol, preferably ethanol. The temperature of the reaction may range from ambient temperature to the boiling point of the solvent. Alternatively, the reaction may be conducted under pressure at a temperature above the boiling point of the solvent, for instance in an autoclave. In that case a suitable temperature is about 180° C. and a suitable pressure about 1930 kPa (280 psi).

Instead of using ammonia in an organic solvent, aqueous ammonia can be employed. Alternatively, the compound of formula (II) may be treated directly with liquid ammonia under pressure, for instance in an autoclave.

The compound of formula (II) is novel. The invention therefore further provides 6-(2,3-dichlorophenyl)-5-chloro-3-thiomethyl-1,2,4-triazine.

The compound of formula (II) may be prepared by treating 6-(2,3-dichlorophenyl)-5-oxo-3-thiomethyl-1,2,4-triazine, which has the formula (III),

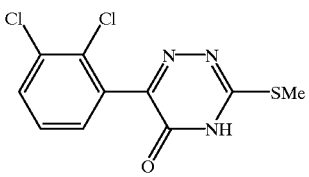

(III)

with a chlorinating agent.

Suitable chlorinating agents include phosphorus oxychloride, thionyl chloride, phosphorus trichloride and phosphorus pentachloride. Phosphorus oxychloride is particularly preferred. The chlorination is of a conventional type and is performed under routine synthetic conditions.

Owing to keto-enol tautomerism, the compound of formula (III) may also exist with the following structure:

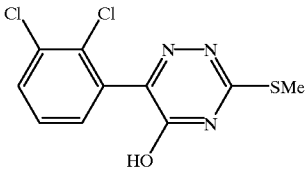

It is to be understood that all references herein to the compound of formula (III) relate to either or both of the keto and enol tautomers.

The compound of formula (III) is novel. The invention therefore further provides 6-(2,3-dichlorophenyl)-5-oxo-3-thiomethyl-1,2,4-triazine.

The compound of formula (III) may be prepared by treating 6-(2,3-dichlorophenyl)-5-oxo-3-thio-1,2,4-triazine of formula (IV)

(IV)

with a methylating agent.

Suitable methylating agents include methyl halides, for instance MeCl, MeBr and MeI, methyl sulphonate and methyl p-toluenesulphonate. Methyl iodide is especially preferred. Methylation is conducted under conventional conditions. For instance, the reaction of the compound of formula (IV) with methyl iodide is preferably carried out in alkaline aqueous solution, e.g. in an aqueous solution of an alkali metal hydroxide such as sodium hydroxide or potassium hydroxide, at ambient temperature.

As with compound (III), compound (IV) exhibits keto-enol tautomerism and may consequently exist with the following structure:

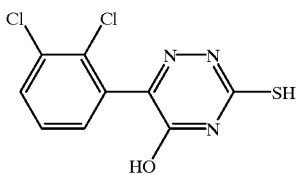

It is to be understood that all references herein to the compound of formula (IV) relate to either or both of the keto and enol tautomers.

The compound of formula (IV) is novel. The invention therefore further provides 6-(2,3-dichlorophenyl)-5-oxo-3-thio-1,2,4-triazine. The compound of formula (IV) may be prepared by treating 2,3-dichlorophenylglyoxylic acid of formula (V)

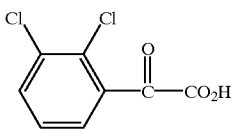

with thiosemicarbazide.

The reaction of the compound of formula (V) with thiosemicarbazide is preferably carried out in alkaline aqueous solution, e.g. in an aqueous solution of sodium hydroxide or potassium hydroxide. It is preferably carried out at a temperature ranging from ambient temperature to the boiling point of the solvent, more preferably at reflux.

The compound of formula (V) ray be prepared by oxidising 2,3-dichloroacetophenone of formula (VI)

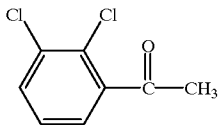

Suitable oxidising agents include selenium dioxide, aqueous alkaline potassium permanganate, potassium dichromate and chromium trioxide, all in the presence of pyridine. The oxidation is performed under conventional conditions.

The compound of formula (VI) may be prepared by treating 1,2-dichlorobenzene with a compound of formula $RM^1$ or $RM^2X$, wherein R represent $C_{1-6}$ alkyl, $M^1$ represents an alkali metal, $M^2$ represents an alkaline earth metal and X represents halogen, followed by the reaction of the compound thus obtained with acetyl chloride or acetic anhydride. $RM^2X$ may, for example, represent a Grignard reagent such as methylmagnesium iodide. A compound of formula $RM^1$ is preferably used, butyl lithium being especially preferred, followed by reaction with acetic anhydride. The reaction is preferably performed at a temperature of about $-70°$ C.

The compound of formula (VI) may also be prepared by treating 2,3-dichlorobenzaldehyde with a compound $RM^1$ or $RM^2X$ wherein R is methyl, preferably with methylmagnesium iodide, and oxidising the α-methyl-2,3-dichlorobenzyl alcohol thus obtained. Suitable oxidising agents include, for example, sodium hypochlorite. The reaction is preferably performed at room temperature.

The compound of formula (VI) may also be prepared by treating 2,3-dichloroiodobenzene with magnesium and treating the compound thus obtained with acetyl chloride in the presence of anhydrous ferric chloride. The reaction is preferably performed at a temperature of about $-70°$ C.

The invention also provides a process which further comprises forming a pharmaceutically acceptable acid addition salt of lamotrigine.

Suitable pharmaceutically acceptable acid addition salts of lamotrigine include the sulphate, phosphate, methanesulphonate, p-toluenesulphonate, benzenesulphonate and isethionate salts. Lamotrigine isethionate is particularly preferred for parenteral administration as it has a high solubility in water.

Lamotrigine isethionate may be prepared by reacting lamotrigine with isethionic acid. Preferably the molar ratio of lamotrigine to isethionic acid is from 1:3 to 3:1, and in particular approximately 1:1.

Isethionic acid is not commercially available and is therefore conveniently made in situ. For example an alkali metal isethionate in solution may be converted to isethionic acid e.g. by passing an aqueous solution of the isethionate through an $H^+$ ion-exchange resin, and the triazine is then mixed with the resulting acid solution. Typically the reaction solvent is water and when this is so the reaction may be performed at temperatures of from 4 to $50°$ C., conveniently at ambient temperature and without the need for any pH adjusters or other additives.

The isethionate salt formed may be recrystallized from e.g. industrial methylated spirit to produce crystals of lamotrigine isethionate which readily dissolve in water.

Alternatively, lamotrigine isethionate may be prepared by reacting a lamotrigine salt other than isethionate with isethionate anion. Preferably the ratio of salt to anion is from 1:50 to 50:1. More preferably the ratio is approximately 1:10. Preferably the reaction is carried out by eluting a solution of the salt in methanol through a column of isethionate anion exchange resin. In this case the salt is preferably lamotrigine methanesulphonate (mesylate).

The invention also provides a process which further comprises preparing a pharmaceutical composition by formulating lamotrigine or a pharmaceutically acceptable acid addition salt thereof with a pharmaceutically acceptable diluent or carrier.

Lamotrigine will be present in the compositions prepared according to the invention in an effective unit dosage form, i.e. in an amount sufficient to be effective against CNS disorders in vivo.

The pharmaceutically acceptable diluent or carrier present in the compositions prepared according to the invention may be a liquid or solid material which is inert or medically acceptable and which is compatible with lamotrigine or its salt.

The pharmaceutical compositions may be given orally or parenterally, used as a suppository, or applied topically as an ointment, cream or powder. However, oral or parenteral administration of the composition is preferred.

For oral administration, fine powders or granules may be used which contain diluting, dispersing and/or surface active agents, and which may be presented in a draught, in water or in a syrup, in capsules or sachets in the dry state or in non-aqueous suspension wherein suspending agents may be included, or in a suspension in water or syrup. Where desirable or necessary, flavouring, preserving, suspending, thickening or emulsifying agents may be included. When a suspension is prepared in water according to the present invention at least one of these agents is preferably present.

For parenteral administration, the active compound may be presented in a sterile aqueous injection solution which may contain anti-oxidants or buffers.

Lamotrigine or a salt thereof may be administered in pure form unassociated with other additives in which case a capsule or sachet is the preferred carrier.

Alternatively the active compound may be presented in pure form as an effective unit dosage, e.g. compressed as a tablet or the like.

Other materials which may be included are, for example, medically inert ingredients, e.g. solid and liquid diluents such as lactose, starch, or calcium phosphate for tablet or capsules; olive oil or ethyl oleate for soft capsules; and water or vegetable oil for suspensions or emulsions; lubricating agents such as talc or magnesium stearate; gelling agents such as colloidal clays; thickening agents such as rum tragacanth or sodium alginate; and other therapeutically acceptable accessory ingredients such as humectants, preservatives, buffers, and antioxidants which are useful as carriers in such formulations.

Tablets and other forms of presentation provided in discrete units may conveniently contain an amount of lamotrigine or a salt thereof which is effective at that dosage or at a multiple of that dosage, e.g. units containing 5 mg to 500 mg, preferably around 10 mg to 250 mg, calculated as the free base.

Aqueous formulations will generally comprise a pharmaceutically acceptable salt of lamotrigine in an amount sufficient to be effective against CNS disorders in vivo and the formulation may be in unit dosage form. Up to about 250 mg/ml of the salt, calculated as free base, may be present in aqueous formulation. However, typical concentrations of the salt in solution are 10 to 70 mg/ml, preferably 10 to 50 mg/ml. For parenteral administration the salt may be presented in sterile aqueous injection solutions which may contain therapeutically acceptable accessory ingredients such as anti-oxidants, buffers and agents to adjust the osmolarity of the solution. Preferably anions such as chloride and phosphates are not present in the solution, since these tend to exchange with the salt to form precipitates.

An aqueous formulation may be prepared by dissolving the salt in aqueous media, suitably sterile water for injection. The solution may be diluted before use to the required concentration.

The following Examples illustrate steps of the process of the invention.

EXAMPLE 1

Preparation of Compound (VI)

Method A

Butyl lithium in hexane (300 ml, 0.474 mol) was added slowly dropwise, with stirring, to 1,2-dichlorobenzene (104.58 g, 0.711 mol) dissolved in dry tetrahydrofuran (2 liters) maintained at a temperature of −70° C., under nitrogen. The resulting solution was stirred at −70° C. for 1 hour. This solution, still at −70° C., was added to acetic anhydride (290.35 g, 2.84 mol), dissolved in dry tetrahydrofuran (1 liter) at −70° C., under nitrogen via a double ended needle. When addition was complete the resulting solution was stirred at −70° C. for approximately 1 hour and allowed to come to room temperature.

The reaction mixture was poured onto ice (5 liters) and after stirring well was allowed to stand overnight at room temperature. The aqueous mixture was extracted with ether (3×1.5 liters). The ether phases were combined, washed with water (3×750 ml), saturated sodium bicarbonate solution (3×750 ml), and brine (1×750 ml). The organic phase was dried over anhydrous magnesium sulphate, filtered and evaporated, to give a yellow liquid. The crude product was put under high vacuum in a got water bath, in order to remove any 1,2-dichlorobenzene and acetic anhydride. 2,3-Dichloroaceto-phenone (67.2 g, 75% yield) was obtained. Ir, nmr and t.l.c. (SiO$_2$;CHCl$_3$) showed the material to contain few impurities, therefore no further purification was attempted.

Method B

Iodomethane (324.89 g, 2.288 mol) was added dropwise, with stirring, to magnesium turnings (54.88 g, 2.288 mol) in dry ether (1 liter), to form methyl magnesium iodide. 2,3-Dichlorobenzaldehyde (200 g, 1.144 mol) dissolved in benzene/diethyl ether (1 liter, 50:50) solution was added dropwise, with stirring, to the Grignard. The reaction mixture was allowed to stir at room temperature overnight. The solution was refluxed for 2 hours, and then allowed to cool. The reaction mixture was poured into saturated ammonium chloride solution (5 liters) and the organic layer separated. The aqueous layer was extracted with ether (3×2 liters). The organic phases were combined, washed with brine (1×2 liters), dried over anhydrous magnesium sulphate, filtered and evaporated down. α-Methyl-2,3-dichlorobenzyl alcohol (196.4 g, 90% yield) was obtained as a yellow oil which crystallised on standing to give a pale-yellow solid. T.l.c. (SiO$_2$;CHCl$_3$) showed no impurities so no further purification was carried out. However, if necessary the alcohol nay be recrystallised from 40–60° C. petroleum ether to afford white prisms of melting point 53° C.

α-Methyl-2,3-dichlorobenzyl alcohol (5.0 g, 0.026 mol) was dissolved in acetic acid (24 ml) and 12% w/v sodium hypochlorite solution (23.26 ml, 0.0314 mol) was added slowly dropwise, with stirring, at a temperature of 15–25° C. When the addition was complete the reaction mixture was stirred at ambient temperature for approximately 1% hours until a starch/iodide test gave a positive result. Saturated sodium bisulphite solution was added to the reaction mixture until the starch/iodide test was negative. The mixture was poured onto ice/brine (100 ml) and extracted with diethyl ether (3×75 ml). The ether phases were combined and washed with 2N sodium hydroxide solution (3×75 ml) until the aqueous washes were alkaline. The ether phase was dried over anhydrous magnesium sulphate, filtered and evaporated down. 2,3-Dichloroacetophenone (3.2 g, 65% yield) was afforded as a pale-yellow oil. T.l.c. (SiO$_2$;CHCl$_3$) and nmr showed this material to contain no impurities.

Method C 2,3-Dichloroiodobenzene (350 g, 1.282 mol) dissolved in dry ether (1250 ml) was added slowly, with stirring, to magnesium turnings (30.77 g, 1.282 mol) in dry diethyl ether (300 ml), in order to form 2,3-dichlorophenylmagnesium iodide under nitrogen. The Grignard was added dropwise, with stirring, to acetyl chloride (301.91 g, 3.846 mol) dissolved in dry diethyl ether (1 liter) and anhydrous ferric chloride (1.925 g, 0.0118 mol) at a temperature of −70° C. under nitrogen. When addition was complete the resulting mixture was stirred at −70° C. for a further 5 minutes, and then allowed to come to room temperature. The reaction mixture was poured onto ice (5 liters) and stirred thoroughly. The aqueous mixture was basified with sodium carbonate and allowed to stand at room temperature overnight. The aqueous solution was extracted with diethyl ether (3×2 liters) and the ether phases combined, dried over anhydrous magnesium sulphate, filtered, and evaporated down. Crude 2,3-dichloroacetophenone (235.7 g) was obtained as a yellow liquid. The crude material was distilled under vacuum to yield pure 2,3-dichloroacetophenone (147.0 g, b.p. 100°

C./2 mmHg; 60.66% yield) Nmr and t.l.c (SiO$_2$;CHCl$_3$) showed the distilled product to contain no impurities.

EXAMPLE 2

Preparation of Compound (V)

A solution of KMnO$_4$ (33.33 g, 0.21 M) in water (1100 ml) was added in dropwise fashion with stirring, over 2 hours, to 2,3-dichloroacetophenone (12.5 g, 0.066 M), KOH (8.33 g, 0.148 M) in water (330 ml), and pyridine (833 ml) at 10–15° C. The resulting mixture was allowed to stir for 1 hour. Excess permanganate was destroyed by the addition of sodium metabisulphite and the resulting solution filtered through hyflo. The filtrate was acidified with concentrated HCl and allowed to stand at room temperature overnight. The acidic solution was extracted with ether and the ether layers combined, filtered and evaporated down to give a product which, after drying over P$_2$O$_5$, was identified as 2,3-dichlorophenylglyoxylic acid of formula (V) by TLC (SiO$_2$:DIPE:HCO$_2$H:H$_2$O). Crude yield=67.8%

EXAMPLE 3

Preparation of Compound (IV)

2,3-Dichlorophenylglyoxylic acid (12.00 g, 0.055 M), the compound of formula (V), was dissolved in warm 1N solution of NaOH (165 ml, 0.165 M). Thiosemicarbazide of formula H$_2$N—NH—C(S)—NH$_2$ (10.12 g, 0.11 M) was dissolved in warm water (175 ml). The two solutions were then mixed and refluxed with stirring for 4 hours. The reaction mixture was allowed to cool overnight and was then acidified at 0.5° C. with concentrated HCl. The resulting suspension was stirred for 30 mins and the solid was filtered off and allowed to dry.

Compound (IV), 6-(2,3-dichlorophenyl)-5-oxo-3-thio-1,2,4-triazine, was obtained in 48% yield. Its identity was confirmed by infra-red spectroscopy and TLC.

EXAMPLE 4

Preparation of Compound (III)

6-(2,3-dichlorophenyl)-5-oxo-3-thio-1,2,4-triazine (16.5 g, 0.06 M), the compound of formula (IV) prepared in Example 3, was dissolved in a solution of 2N NaOH (33.32 ml). To this was added methyl iodide (25.55 g, 0.18 M) in water (50 ml). The resulting solution was stirred overnight at room temperature. The solid which formed was filtered off, dissolved in 2N NaOH and acidified with concentrated HCl to give a precipitate which was filtered at the pump and dried over P$_2$O$_5$ to give compound (III), 6-(2,3-dichlorophenyl)-5-oxo-3-thiomethyl-1,2,4-triazine (10.85 g, 63% yield). Melting point=131.6° C.

EXAMPLE 5

Preparation of Compound (II)

6-(2,3-Dichlorophenyl)-5-oxo-3-thiomethyl-1,2,4-triazine (2.0 g, 0.0069 M), which is compound (III), and phosphorus oxychloride (POCl$_3$, 40 ml) were placed together in a flask and heated at reflux for 2 hours. The reaction mixture was allowed to cool and excess POCl$_3$ was removed by evaporation. The residue was dissolved in CHCl$_3$ and made alkaline with NH$_4$OH. After standing for 30 minutes the resulting mixture was washed with water, filtered and evaporated down to give compound (II), 6-(2,3-dichlorophenyl)-5-chloro-3-thiomethyl-1,2,4-triazine in 80% yield. Its purity was confirmed by TLC.

EXAMPLE 6

Preparation of Lamotrigine

The 6-(2,3,-dichlorophenyl)-5-chloro-3-thiomethyl-1,2,4-triazine prepared in Example 5 was dissolved in ethanol (100 ml) saturated with ammonia gas and heated in a sealed glass tube in an autoclave at 180° C./1930 kPa (280 p.s.i.) for 72 hours.

The total contents of the tube was evaporated down to give a dark brown crude product. The crude product was recrystallised from methanol and identified as compound (I), 3,5-diamino-6-(2,3-dichlorophenyl)-1-2,4-triazine (lamotrigine) by TLC (Rf=0.20). Melting point=218° C.

EXAMPLE 7

Preparation of 3,5-diamino-6-(2,3-dichlorophenyl)-1,2,4-triazine Isethionate

A solution of sodium isethionate (148 g, 1.0 mol) in water (4.9 liters) was passed down a column of IR 120 (H) ion-exchange resin and eluted with water. 3,5-Diamino-6-(2,3-dichlorophenyl)-1,2,4-triazine (256 g, 1.0 mol) was dissolved in the resulting isethionic acid, and the solution filtered and evaporated in vacuo. The residue was recrystallised from industrial methylated spirit to afford 3,5-diamino-6-(2,3-dichlorophenyl)-1,2,4-triazine isethionate.

Yield 273.3 g (72%), m.p. 242° C.

EXAMPLE 8

Preparation of 3,5-diamino-6-(2,3-dichlorophenyl)-1,2,4-triazine Isethionate 50 mmol of Amberlite (trade mark) IR-45 (OH) was mixed with 15 mmol (10 ml) aqueous isethionic acid and the resulting material was packed into a column. The column was then washed with methanol. 0.7 g (2 mmol) of a methanolic solution of 3,5-diamino-6-(2,3-dichlorophenyl)-1,2,4-triazine mesylate was eluted through the column. The elutant was evaporated in vacuo and the residue was recrystallised from industrial methylated spirit and gave 3,5-diamino-6-(2,3-dichlorophenyl)-1,2,4-triazine isethionate:

Yield 300 mg (40%), m.p. 242–243° C.

EXAMPLE 9

74.625 g (0.195 mol) of 3,5-diamino-6-(2,3-dichlorophenyl)-1,2,4-triazine isethionate was added to and dissolved in around 900 ml of water for injections BP, and diluted to 1000 ml with further water for injections BP, to give an aqueous solution containing isethionate salt equivalent to 50 mg/ml of the 3,5-diamino-6-(2,3-dichlorophenyl)-1,2,4-triazine base. This solution was acceptable on tonicity grounds.

EXAMPLE 10

14.925 (0.039 mol) of 3,5-diamino-6-(2,3-dichlorophenyl)-1,2,4-triazine isethionate was added to a solution of 43.8 g (0.221 mol) of dextrose monohydrate in around 900 ml of water for injections BP and diluted to 1000 ml with further water for injections BP, to give an aqueous solution containing isethionate salt equivalent to 10 mg/ml of the 3,5-diamino-6-(2,3-dichlorophenyl)-1,2,4-triazine base. This solution was acceptable on tonicity grounds.

EXAMPLE 11

A pharmaceutical composition having the following ingredients was prepared.

| | |
|---|---|
| 3,5-Diamino-6-(2,3-dichlorophenyl)-1,2,4-triazine | 150 mg) |
| Lactose | 200 mg) |
| Maize Starch | 50 mg) |
| Polyvinylpyrrol idone | 4 mg) |
| Magnesium Stearate | 4 mg) |

) contents per tablet

The drug was mixed with the lactose and starch and granulated with a solution of the polyvinylpyrrolidone in water. The resultant granules were dried, mixed with magnesium stearate and compressed to give tablets of average weight 408 mg.

I claim:

1. A process for the preparation of lamotrigine of formula (I)

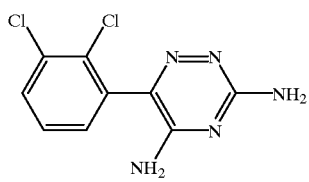
(I)

which comprises treating 6-(2,3-dichlorophenyl)-5-chloro-3-thiomethyl-1,2,4-triazine of formula (II)

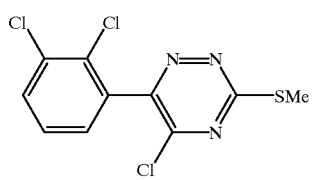
(II)

with ammonia.

2. A process according to claim 1 wherein the compound of formula (II) is prepared by treating the compound of formula (III)

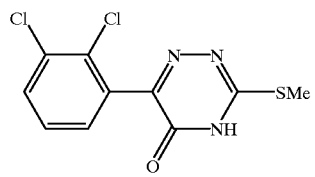
(III)

with a chlorinating agent.

3. A process according to claim 2, wherein the compound of formula (III) is prepared by treating the compound of formula (IV)

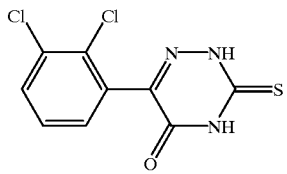
(IV)

with a methylating agent.

4. A process according to claim 3 wherein the compound of formula (IV) is prepared by treating the compound of formula (V)

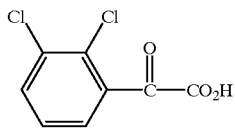
(V)

with thiosemicarbazide.

5. A process according to claim 1 which further comprises forming a pharmaceutically acceptable acid addition salt of lamotrigine.

6. 6-(2,3-Dichlorophenyl)-5-chloro-3-thiomethyl-1,2,4-triazine.

7. 6-(2,3-Dichlorophenyl)-5-oxo-3-thiomethyl-1,2,4-triazine.

8. 6-(2,3-Dichlorophenyl)-5-oxo-3-thio-1,2,4-triazine.

* * * * *